United States Patent
Firmbach et al.

(10) Patent No.: US 12,383,281 B2
(45) Date of Patent: Aug. 12, 2025

(54) SURGICAL INSTRUMENT

(71) Applicant: Aesculap AG, Tuttlingen (DE)

(72) Inventors: Franz-Peter Firmbach, Emmingen-Liptingen (DE); Svenja Anhorn, Heroldstatt (DE); Martin Nonnenmann, Wurmlingen (DE)

(73) Assignee: Aesculap AG, Tuttlingen (DE)

( * ) Notice: Subject to any disclaimer, the term of this patent is extended or adjusted under 35 U.S.C. 154(b) by 269 days.

(21) Appl. No.: 18/348,690

(22) Filed: Jul. 7, 2023

(65) Prior Publication Data
US 2024/0023973 A1  Jan. 25, 2024

(30) Foreign Application Priority Data
Jul. 25, 2022 (DE) ..................... 10 2022 207 578.1

(51) Int. Cl.
*A61B 17/15* (2006.01)
(52) U.S. Cl.
CPC .................. *A61B 17/157* (2013.01)
(58) Field of Classification Search
CPC .. A61B 17/157; A61B 17/155; A61B 17/1764
See application file for complete search history.

(56) References Cited

U.S. PATENT DOCUMENTS

| | | |
|---|---|---|
| 10,709,458 B1 | 7/2020 | Bini et al. |
| 2008/0103506 A1* | 5/2008 | Volpi ................. A61B 17/1764 606/96 |
| 2015/0045801 A1 | 2/2015 | Axelson, Jr. et al. |
| 2017/0333018 A1 | 11/2017 | Sehat |
| 2018/0140440 A1 | 5/2018 | Jackson et al. |
| 2019/0336141 A1 | 11/2019 | Erickson et al. |
| 2021/0000484 A1 | 1/2021 | Goble et al. |

FOREIGN PATENT DOCUMENTS

| | | |
|---|---|---|
| GB | 2558543 A | 7/2018 |
| WO | 2011018647 A1 | 2/2011 |

* cited by examiner

*Primary Examiner* — Samuel S Hanna
(74) *Attorney, Agent, or Firm* — Christopher A. Rothe; CM Law (57) ABSTRACT

A surgical instrument for use in knee joint replacement surgery includes a first fastening device for fastening to a reference component attached to a distal femur, a second fastening device spaced apart distally from the first fastening device for fastening to a tibial cutting block for cutting guidance on a proximal tibia, a circular arc guide connected to the first and second fastening devices by which the second fastening device is movable relative to the first fastening device and guided in a sagittal guide plane, a first linear guide by which the circular arc guide is connected to the first fastening device and movable relative thereto guided in the guide plane along a first guide path, and a second linear guide by which the second fastening device is connected to the circular arc guide and movable relative thereto and guided in the guide plane along a second guide path.

12 Claims, 4 Drawing Sheets

SURGICAL INSTRUMENT

CROSS-REFERENCE TO RELATED APPLICATION(S)

This application claims priority under 35 U.S.C. § 119 to German Application No. 10 2022 207 578.1, filed on Jul. 25, 2022, the content of which is incorporated by reference herein in its entirety.

FIELD

The present disclosure relates to a surgical instrument for use in a knee joint replacement operation.

BACKGROUND

The use of orthopedic prostheses as artificial replacements for damaged or worn natural bone structures is common medical practice. In particular, hip joint and knee joint replacement operations are nowadays routine in surgical orthopedics.

In a knee joint replacement operation, or total knee arthroplasty (TKA), joint surfaces of the femur and/or tibia that have become worn or have been otherwise affected by disease or by injury are replaced by a knee joint prosthesis. Such knee joint prostheses usually comprise a femoral component, which is implanted at the distal end of the femur, and a tibial component, which is implanted at the proximal end of the tibia. To ensure proper functioning of the artificial replacement joint, the aforementioned components have to be placed as precisely as possible in a defined position and orientation with respect to the anatomy of the patient and to the axes of the patient's body. Otherwise, an unsatisfactory result must be expected. There are different surgical approaches as regards the positioning of the components.

In an approach known as mechanical alignment, which has been the approach mainly used hitherto, the position and orientation of the artificial joint axes of the knee joint prosthesis have been provided so as to be mechanically ideal, without consideration being given to any orthopedic deformities presented by the patient. The longitudinal axis of the tibia has often been used here as a reference axis for the orientation and positioning. Clinical studies have shown that the mechanical alignment approach can lead to the function of the artificial knee joint being felt unnatural.

A further approach is what is known as kinematic alignment. In this technique, the femoral component and the tibial component are positioned taking into consideration any orthopedic deformities presented by the patient. The aim is to restore the patient's natural joint orientation, which in some cases is affected by deformities. Clinical studies have shown that the kinematic alignment approach is often associated with improved patient satisfaction. In particular, the function of the artificial knee joint is felt by the patient to be more natural.

Aiming at further improving patient satisfaction, there is a fundamental need for surgical instruments that are as precise as possible, easy to use and cost effective for the implementation of kinematic alignment.

The present disclosure relates to such surgical instruments, especially to a surgical instrument for positioning a tibial cutting block on the proximal tibia. Such instruments are also referred to as a transfer tool or tibia transfer tool and permit transfer of a varus/valgus alignment (V/V alignment below), which has already been determined on the femur side, to the tibia. Different instruments of this type are known from the prior art.

For example, GB 2558543 A discloses an instrument with an extension arm. The extension arm can be fastened at one end to a femoral reference component. The reference component in particular defines the V/V alignment. The V/V alignment can be transferred to the proximal tibia by means of the extension arm. The length of the extension arm defines a proximodistal position of the tibial cutting block and therefore of the proximal tibial cut (tibial cutting height below). The transfer is undertaken in an extension position, i.e. with the leg stretched.

A further instrument is known from US 2019/0336141 A1 and is fastenable at one end to a 4-in-1 femoral cutting block and at the other end to a tibial cutting block. To adjust the tibial cutting height, the known instrument has a type of linear guide. The transfer is undertaken in a flexion position, i.e. with the leg flexed.

U.S. Pat. No. 10,709,458 B1 discloses further transfer tools which permit a transfer in an extension or flexion position.

SUMMARY

It is the object of the present disclosure to make available a surgical instrument which affords advantages over the prior art and in particular permits improved positioning of the tibial cutting block on the basis of a femorally fixed reference component.

The surgical instrument according to the present disclosure has: a first fastening device which is configured for releasably fastening to a reference component attached to a distal femur, a second fastening device which is spaced apart distally from the first fastening device and is configured for releasably fastening to a tibial cutting block for cutting guidance on a proximal tibia, a circular arc guide which is connected at one end to the first fastening device and at the other end to the second fastening device and by means of which the second fastening device is linearly movable relative to the first fastening device guided in a sagittal guide plane along a guide path which is elongate in the manner of a circular arc (i.e. a circular-arc-shaped guide path), a first linear guide, by means of which the circular arc guide is connected at one end to the first fastening device and is linearly movable relative thereto guided in the guide plane along a first guide path which is elongate anteroposteriorly, and a second linear guide, by means of which the second fastening device is connected at the other end to the circular arc guide and is linearly movable relative thereto guided in the guide plane along a second guide path which is elongate anteroposteriorly. The surgical instrument according to the present disclosure permits improved positioning of the tibial cutting block. The improved positioning is achieved by interaction of the circular arc guide, the first linear guide and the second linear guide. When the surgical instrument is in use, the first fastening device is fastened releasably to the femorally attached reference component, and the tibial cutting block is fastened releasably to the second fastening device. The reference component is, for example, a distal femoral cutting block for distal cutting guidance on the femur or the like. Neither the reference component nor the tibial cutting block are parts of the surgical instrument according to the present disclosure. The circular arc guide permits a guided circular-arc-shaped movement of the second fastening device relative to the first fastening device. When the surgical instrument is in use, the circular arc guide consequently permits an accordingly guided relative movement of the tibial cutting block in relation to the femoral reference component. By this means, the inclination of the tibial cutting block in the guide plane can be adjusted. The guide plane is aligned sagittally and consequently extends anteroposteriorly and proximodistally. Said inclination is also referred to as a posterior or anterior slope. The adjustability of the inclination of the tibial cutting block (slope for short below) firstly permits adaptation to preoperatively defined parameters. Secondly, an actually prevailing flexion or extension position of the leg can be taken into consideration and compensated for by the movability of the circular arc guide. The circular arc guide is movable relative to the first fastening device along the first guide path. By this means, an anteroposterior position of the circular-arc-shaped guide path in relation to the first fastening device—and therefore the reference component—can be changed and adapted to the anatomy of the patient. In an ideal case, the position of the circular-arc-shaped guide path is adapted in such a manner that the circle center point thereof comes to lie on the mechanical tibial axis. This ensures that an adjustment of the slope does not simultaneously lead to an undesired change in a proximodistal position of the tibial cutting block and therefore of the tibial cutting height. The second fastening device is movable relative to the circular arc guide along the second guide path. This ensures that an anteroposterior position of the second fastening device—and therefore that of the tibial cutting block—can be adapted to the anatomy of the patient, in particular to the size of the tibia, without there being an undesired change in the anteroposterior position of the circular-arc-shaped guide path.

The position and direction designations used in this description relate to the body of a patient, in particular the femur of the patient, and to this extent they are to be understood in accordance with their usual anatomical meaning. Consequently, "anterior" denotes front or lying to the front, "posterior" denotes rear or lying to the rear, "medial" denotes inner or lying to the inside, "lateral" denotes outer or lying to the outside, "proximal" denotes toward the center of the body, and "distal" denotes away from the center of the body. Furthermore, "proximodistal" denotes along, preferably parallel to, a proximal-distal axis, "anteroposterior" denotes along, preferably parallel to, an anterior-posterior axis, and "mediolateral" denotes along, preferably parallel to, a medial-lateral axis. The aforementioned axes are orthogonal to one another and can of course be understood in relation to X, Y and Z axes not associated with the anatomy of the patient. For example, the proximal-distal axis can be designated alternatively as the X axis. The medial-lateral axis can be designated as the Y axis. The anterior-posterior axis can be designated as the Z axis. For the sake of better illustration and simplicity of the designations, the aforementioned anatomical position and direction designations are primarily used in the following.

In one embodiment, an alignment rod is present and is configured for aligning on an anterior edge of the tibia, wherein the alignment rod is mounted at one end on the second fastening device so as to be pivotable relative to the second fastening device about a pivot axis oriented orthogonally to the guide plane. The alignment rod permits referencing at the aforementioned anterior edge, which can also be referred to as the tibia front edge. The slope (anterior or posterior inclination of the tibial cut) is often preoperatively defined with respect to the tibia front edge. The alignment rod permits simple monitoring of the slope with respect to the tibia front edge. The alignment rod is elongate between a first end and a second end. The first end is mounted pivotably on the second fastening device. The second end faces distally away from the second fastening device.

In one embodiment, a first indicating device is present and is configured for indicating a first angular position of the second fastening device with respect to the circular-arc-shaped guide path, and/or a second indicating device is present and is configured for indicating a second angular position of the alignment rod with respect to the pivot axis. The first indicating device serves for indicating the relative sagittal inclination between the first fastening device and the second fastening device. When the surgical instrument is in use—with the first fastening device fastened femorally and the tibial cutting block fastened to the second fastening device—the first indicating device displays the slope of the tibial cutting block and therefore also the tibial cut. The second indicating device serves for indicating a relative sagittal inclination between the alignment rod and the second fastening device. When the surgical instrument is in use, a deviation in the flexion/extension position can be determined by means of the second indicating device. The determined deviation can be compensated for subsequently via a corresponding adjustment of the slope. For this purpose, the slope is initially adjusted to 0°. This can take place via a corresponding movement of the second fastening device along the guide path which is elongate in the shape of a circular arc. The alignment rod can then be aligned parallel to the anterior edge of the tibia. The second angular position arising in this case is displayed by means of the second indicating device. The first angular position can accordingly be corrected by the value of the second angular position. This results in an actual slope of 0°, irrespective of a possible deviation from the precise extension. The slope can subsequently be adjusted once again to a preoperatively defined value. The first indicating device is preferably a scale provided on the circular arc guide. The second indicating device is preferably a scale arranged on the alignment rod and/or the second fastening device. The scales preferably each have a reading mark and scale lines for indicating and/or reading the respective angular position. Alternatively, it is conceivable for the first angular position and/or the second angular position to be detected by means of sensors suitable for this purpose and indicated digitally. Accordingly, the first indicating device and/or the second indicating device can also be configured as a display.

In one embodiment, the circular arc guide has at least one curved guide rod and a guide receptacle in which the guide rod is accommodated in a slidably guided manner, wherein the guide receptacle is connected to the first linear guide and the guide rod to the second linear guide, or vice versa. The guide rod is substantially elongate proximodistally and curved posteriorly concavely and/or anteriorly convexly with respect to a viewing direction directed mediolaterally. The curvature of the guide rod and/or of the guide receptacle defines the guide path which is elongate in the shape of a circular arc. The same accordingly applies to the guide receptacle. To avoid undesired rotation about the longitudinal axis of the guide rod, the guide rod preferably has a cross section which is not rotationally symmetrical. The same accordingly applies to the guide receptacle in which the guide rod is accommodated. In one embodiment, the guide receptacle is connected to the first linear guide and the guide rod is connected to the second linear guide. In a further embodiment, the guide rod is connected to the first linear guide and the guide receptacle is connected to the second linear guide.

In one embodiment, the guide receptacle is connected to the first linear guide and has a guide element, in particular a cylinder element or a cylinder receptacle, of same, and/or the guide rod is connected to the second linear guide and has a guide element, in particular a slotted guide block or a slotted guide slot, of same. The guide receptacle is connected to the aforementioned guide element of the first linear guide fixedly and/or immovably relative thereto. In one embodiment, the guide element of the first linear guide is a cylinder element, in a further embodiment a cylinder receptacle in which the cylinder element is guided slidably along the first guide path. The guide rod is connected to the aforementioned guide element of the second linear guide fixedly and/or immovably relative thereto. In one embodiment, the guide element of the second linear guide is a slotted guide block, in a further embodiment a slotted guide slot, in which the slotted guide block is guided slidably along the second guide path.

In one embodiment, the first linear guide is a cylinder guide and has at least one cylinder element, which is elongate anteroposteriorly, and a cylinder receptacle in which the cylinder element is accommodated in a slidably guided manner. The longitudinal extent of the cylinder element and/or of the cylinder receptacle defines the first guide path. The cylinder guide permits a slidable relative displacement of the circular arc guide with respect to the first fastening device and therefore—when the surgical instrument is in use—with respect to the reference component. This embodiment of the first linear guide is particularly robust and exact. To avoid an undesired rotation about the longitudinal axis of the cylinder element and/or of the cylinder receptacle, the cylinder element preferably has a cross section which is not rotationally symmetrical. The same preferably applies accordingly to the cylinder receptacle. Alternatively, the cylinder element and/or the cylinder receptacle can have a circular cross section. In order in this case to prevent undesired rotation about the longitudinal axis, the cylinder guide preferably has two cylinder elements and cylinder receptacles arranged spaced apart mediolaterally.

In one embodiment, the cylinder element is connected immovably to the first fastening device, and the cylinder receptacle is connected immovably to the circular arc guide, preferably to the guide receptacle thereof. This achieves further simplified construction of the surgical instrument.

In one embodiment, the second linear guide is a slotted guide mechanism and has a slotted guide block and a slotted guide slot which is elongate anteroposteriorly and in which the slotted guide block is accommodated in a slidably guided manner. The slotted guide slot defines the second guide path. Since the second linear guide is movable together with the second fastening device along the circular-arc-shaped guide path, the orientation of the elongate slotted guide slot changes accordingly. The orientation of the slotted guide slot is at least substantially anteroposterior irrespective of the position of the second fastening device along the circular-arc-shaped guide path.

In one embodiment, the slotted guide block is connected immovably to the circular arc guide, preferably to the guide rod thereof, and the slotted guide slot is formed on the second fastening device. By this means, a further simplified construction of the surgical instrument is achieved. The slotted guide block is preferably arranged and/or formed at an end of the guide rod facing away from the first fastening device. The slotted guide block is preferably formed integrally at the aforementioned end of the guide rod.

In one embodiment, the first fastening device has at least one plug-in element which is configured for releasably plugging together with a complementary reference geometry of the reference component. By this means, the first fastening device can be releasably fastened in a particularly simple manner to the reference component. In one embodiment, the reference component is a distal femoral cutting block which is configured for receiving and guiding a sawblade in applying a distal femoral cut. For this purpose, the femoral cutting block has at least one receiving slot for the aforementioned sawblade. The at least one plug-in element is preferably configured for plugging into the guide slot. In this embodiment, the guide slot forms the complementary reference geometry.

In one embodiment, the second fastening device has a main body on which main body are arranged: a fastening element, which is configured for releasably fastening to a fastening portion, provided for this purpose, of the tibial cutting block, a guide element of the second linear guide, preferably the slotted guide slot thereof, and the alignment rod. This achieves a further simplified construction of the surgical instrument. The fastening element is designed differently in different embodiments and can be, for example, a clamping, latching, plug-in and/or snap-fit element for releasably fastening to the tibial cutting block. In one embodiment, the fastening element can be shifted relative to the main body between a fastening position and a release position. In the fastening position, the second fastening device and the tibial cutting block are connected releasably to each other by means of the fastening element. In the release position, the second fastening device is released from the tibial cutting block, and vice versa. The alignment rod is mounted on the main body so as to be pivotable about the pivot axis relative thereto. If there is a second indicating device for indicating a second angular position of the alignment rod with respect to the pivot axis according to one of the preceding embodiments, said indicating device is preferably arranged as a scale on the main body and/or on the alignment rod.

In one embodiment, a fixing device is present and is configured for fixing the movability of the circular arc guide. The second fastening device can be fixed immovably relative to the first fastening device along the circular-arc-shaped guide path by means of the fixing device. This counteracts an undesired shifting of the second fastening device along the circular-arc-shaped guide path. When the surgical instrument is in use, the fixing device counteracts an undesired adjustment of the slope. The fixing device acts in a form-fitting and/or force-fitting manner between different components and/or portions of the circular arc guide. If the circular arc guide has a guide rod and a guide receptacle, the aforementioned components can be fixed relative to one another by means of the fixing device.

The present disclosure furthermore relates to a surgical instrument system comprising a surgical instrument according to the preceding description, a reference component, which is fastened releasably to the first fastening device of the surgical instrument, and a tibial cutting block, which is fastened releasably to the second fastening device of the surgical instrument.

BRIEF DESCRIPTION OF THE DRAWINGS

Further advantages and features of the present disclosure will become clear from the following description of a preferred exemplary embodiment of the present disclosure, which is illustrated with reference to the drawings.

DETAILED DESCRIPTION

According to FIGS. 1 to 5, a surgical instrument 1 is provided for use in a knee joint replacement operation. The surgical instrument 1 can also be referred to as a transfer tool or tibia transfer tool and serves for a referenced positioning of a tibial cutting block 700 on a proximal tibia T. A distal femoral cutting block 600 which is already positioned on a distal femur F is used as reference for the position of the tibial cutting block 700. Neither the femoral cutting block 600 nor the tibial cutting block 700 are part of the surgical instrument 1. The surgical instrument 1 is releasably connectable in a manner still to be described in detail on one side to the femoral cutting block 600 and on the other side to the tibial cutting block 700. Together with the two cutting blocks 600, 700, the surgical instrument 1 forms a surgical instrument system 10. The surgical instrument 1 has a first fastening device 100, a second fastening device 200, a circular arc guide 300, a first linear guide 400, and a second linear guide 500.

The first fastening device 100 is configured for releasably fastening to the distal femoral cutting block 600. The femoral cutting block 600 serves to this extent as a reference component for referencing the position and alignment of the tibial cutting block 700.

The second fastening device 200 is spaced apart distally from the first fastening device 100 and configured for releasably fastening to the tibial cutting block 700.

The circular arc guide 300 is connected at one end to the first fastening device 100 and at the other end to the second fastening device 200. The connections are in each case indirect. In this case, the circular arc guide 300 is connected at one end to the first fastening device 100 by means of the first linear guide 400. At the other end, the circular arc guide 300 is connected to the second fastening device 200 by means of the second linear guide 500. The circular arc guide 300 has a guide path C which is elongate in the shape of a circular arc. The circular-arc-shaped guide path C (also circular guide path below) is arranged in a guide plane E. The guide plane E runs proximodistally and anteroposteriorly. The guide plane E is a sagittal plane. The circular arc guide 300 permits guided relative movability between the second fastening device 200 and the first fastening device 100. The second fastening device 200 is linearly movable relative to the first fastening device 100 in a manner guided along the circular guide path C. The second fastening device 200 executes a rotation and/or pivoting movement about a center point M of the circular guide path C. The center point M lies spaced apart posteriorly from the circular guide path C. In other words, the circular guide path C is curved posteriorly concavely and anteriorly convexly. The center point M can be positioned in a manner still to be described in detail relative to joint axes of the patient, specifically to the tibial axis (without reference sign).

The first linear guide 400 is connected at one end to the first fastening device 100 and at the other end to the circular arc guide 300. The first linear guide 400 establishes a relatively movable connection between the first fastening device 100 and the circular arc guide 300. The first linear guide 400 has a first guide path L1. The first guide path L1 is elongate anteroposteriorly and arranged in the guide plane E and/or offset parallel thereto. The first guide path L1 is elongate rectilinearly.

The second linear guide 500 is connected at one end to the circular arc guide 300 and at the other end to the second fastening device 200. The second linear guide 500 establishes a relatively movable connection between the circular arc guide 300 and the second fastening device 200. The second linear guide 500 has a second guide path L2. The second guide path L2 is elongate rectilinearly. The second guide path L2 is arranged in the guide plane E and/or is offset parallel thereto. In the intraoperative situation shown with reference to FIG. 1, the second guide path L2 is elongate parallel to the first guide path L1 and therefore anteroposteriorly. In the embodiment shown, the orientation of the second guide path L2 is dependent on the position of the second fastening device 200 along the circular guide path C.

By means of the interaction of the circular arc guide 300, the first linear guide 400 and the second linear guide 500, the tibial cutting block 700 can be positioned on the tibia T starting from the positioned femoral cutting block 600 in an improved manner in comparison to the prior art. Firstly, the sagittal inclination of the tibial cutting block 700 can be adjusted in a manner still to be described in detail without an undesired effect on what is referred to as the tibial cutting height. The sagittal inclination is also referred to as a slope. The tibial cutting block 700 is positioned here in extension, i.e. with the leg and/or knee joint stretched. In extension, the femur F and the tibia T enclose an angle of 180°. Deviations from the precise extension during the adjustment of the slope can be taken into consideration by means of the surgical instrument 1.

Before further details of the function of the surgical instrument 1 and the use thereof are described, first of all the further design of the surgical instrument 1 will be explained in detail.

In the embodiment shown, the first fastening device 100 has a plug-in element 101 which is configured for releasably plugging together with a reference geometry of the femoral cutting block 600. The femoral cutting block 600 serves to apply a distal femoral cut and may also be referred to as femoral saw block or distal femur cutting jig. The design and functioning of the femoral cutting block 600 are known in principle to a person skilled in the art. The femoral cutting block 600 has a guide slot 601 which is used here as reference geometry. The guide slot 601 is configured for receiving and guiding a medical sawblade for the distal resection of the femur F and is conventionally aligned parallel to a distal condyle line of the femur F within the scope of the kinematic alignment approach. For fastening the surgical instrument 1 to the femoral cutting block 600, the plug-in element 101 can be plugged into the guide slot 601 thereof. Such a state is shown with reference to FIGS. 1 to 5. For this purpose, dimensions of the plug-in element 101 match with dimensions of the guide slot 601. In the plugged-in state, the plug-in element 101 is held in a form-fitting manner in the guide slot 601 mediolaterally, proximodistally and posteriorly. To release the fastening, the plug-in element 101 can be pulled anteriorly out of the guide slot 601.

In the embodiment shown, the first linear guide 400 is a cylinder guide Z and has at least one cylinder element 401, which is elongate along the first guide path, and a cylinder receptacle 402, which is elongate coaxially with respect thereto. The cylinder element 401 is accommodated in the cylinder receptacle 402 so as to be slidable along the first guide path L1.

In the present case, the cylinder element 401 is connected fixedly and/or (relatively) immovably to the first fastening device 100, more precisely: to the plug-in element 101 thereof. The cylinder receptacle 402 is connected fixedly and/or (relatively) immovably to the circular arc guide 300. In an embodiment which is not shown in the Figures, a reverse arrangement thereto is provided.

The cylinder element 401 and the cylinder receptacle 402 each have a circular-cylindrical cross section. To counteract an undesired rotation of the cylinder guide Z about its longitudinal axis, a further cylinder element 401' and a further cylinder receptacle 402' are provided here. The further cylinder element 401' and the further cylinder receptacle 402' are arranged spaced apart medially from the cylinder element 401 and the cylinder receptacle 402. Otherwise, the functioning and design thereof are identical. Further explanations regarding the further cylinder element 401' and the further cylinder receptacle 402' are therefore unnecessary. In an embodiment which is not shown in the Figures, the cylinder guide has cross sections which are not rotationally unsymmetrical in order to counteract an undesired rotation about the first guide path.

In the embodiment shown, the circular arc guide 300 has a curved guide rod 301 and a guide receptacle 302 curved in a complementary manner. The guide rod 301 is accommodated in the guide receptacle 302 so as to be slidable along the circular guide path C.

In the embodiment shown, the guide receptacle 302 is connected to the first fastening device 100 fixedly and/or immovably with respect to the circular guide path C. Accordingly, the guide rod 301 is movable with respect to the first fastening device 100 relative to the circular guide path C. Both the guide rod 301 and the guide receptacle 302 are movable with respect to the first fastening device 100 relative to the first guide path L1.

In the embodiment shown, the guide receptacle 302 has a U-shaped cross section with mediolaterally opposite limbs 3021, 3022. The limbs 3021, 3022 may also be referred to as lateral limb 3021 and medial limb 3022. The guide rod 301 is held in a form-fitting manner mediolaterally between the two limbs 3021, 3022. In the embodiment shown, the guide receptacles 402, 402' of the cylinder guide Z are connected fixedly and/or immovably to the guide receptacle 302. In the present case, the guide receptacle 302 and the two cylinder receptacles 402, 402' form a common, integral component.

The guide rod 301 is elongate in a curved manner between a proximal end and a distal end (without reference signs. The proximal end is held slidably in the guide receptacle 302. The distal end is connected to the second fastening device 200 so as to be movable relative thereto along the second guide path L2 by means of the second linear guide 500.

In the present case, the circular arc guide 300 also has a fixing device 303 which is configured for fixing the movability of the circular arc guide 300. The relative movability between the guide rod 301 and the guide receptacle 302 can be optionally fixed and released by means of the fixing device 300. Consequently, the fixing device 303 counteracts an inadvertent relative movement along the circular guide path C. The fixing device 303 brings about a releasable force-fitting and/or form-fitting connection between the guide rod 301 and the guide receptacle 302. For example, the fixing device 303 can bring about bracing of the limbs 3021, 3022 in relation to the guide rod 301. For this purpose, the fixing device 302 can have a screw mechanism, clamping mechanism, latching mechanism or some other mechanism. Further details regarding the functioning and regarding the construction of the fixing device 303 are not essential for the present disclosure. A more detailed explanation of the fixing device 303 is therefore considered to be unnecessary.

Furthermore, the circular arc guide 300 here has a first indicating device A1. In the embodiment shown, the first indicating device A1 is a scale with scale lines which are not denoted specifically and are provided here on the guide rod 301. A distal front edge, not denoted specifically, of the guide receptacle 302 can serve as a reading mark. During a relative movement between the guide rod 301 and the guide receptacle 302, the reading mark migrates along the scale lines. The first indicating device A1 consequently indicates a relative position between the guide rod 301 and the guide receptacle 302 with respect to the circular guide path C. When the surgical instrument 1 is in use, the first indicating device A1 consequently indicates a first angular position $\alpha 1$ of the second fastening device 200—and therefore also of the tibial cutting block 700—with respect to the circular-arc-shaped guide path C. In other words, the first indicating device A1 serves to indicate the sagittal inclination, i.e. the slope, of the tibial cutting block 700.

In the embodiment shown, the second linear guide 500 is a slotted guide mechanism K. The slotted guide mechanism K has a slotted guide block 501 (see in particular FIG. 3) and a slotted guide slot 502. The slotted guide slot 502 is elongate along the second guide path L2. The slotted guide block 501 is held in the slotted guide slot 502 so as to be slidable along the second guide path L2.

In the embodiment shown, the slotted guide block 501 is connected to the circular arc guide 300 fixedly and/or (relatively) immovably. The slotted guide slot 502 is connected to the second fastening device 200 fixedly and/or (relatively) immovably. Specifically, the slotted guide block 502 is connected fixedly to the distal end (without reference sign) of the guide rod 301. The slotted guide slot 502 is open at one end, at its anterior end (without reference sign). The slotted guide block 501 can be introduced through the open end into the slotted guide slot 502 and removed from same. By this, assembly and disassembly of the surgical instrument 1, for example for cleaning, sterilizing or the like, are simplified.

In the embodiment shown, the second fastening device 200 has a main body 201. The slotted guide slot 502 is formed here on the main body 201. For the actual fastening of the tibial cutting block 700 to the second fastening device 200, the latter has a fastening element 202. The fastening element 202 interacts releasably in a force-fitting and/or form-fitting manner with a section of the tibial cutting block 700 provided for this purpose. In the present case, the fastening element 202 is mounted on the main body 201 relative thereto between a fastening position and a release position. In the fastening position, the tibial cutting block 700 is connected releasably to the main body 201 by means of the fastening element 202. In the release position, the tibial cutting block 700 is released relative to the main body 201, and vice versa.

In the embodiment shown, the surgical instrument furthermore has an alignment rod 800. The alignment rod 800 is configured for aligning on an anterior edge V of the tibia T. The anterior edge V may also be referred to as tibia front edge. The alignment rod 800 is mounted at one end on the second fastening device 200 so as to be pivotable relative to the second fastening device 200 about a pivot axis S oriented orthogonally to the guide plane E. In the embodiment shown, the alignment rod 800 is mounted on the main body 201. The alignment rod 800 is elongate between a proximal end 801 and a distal end 802 (not shown in detail). The pivotable mounting permits an alignment of the alignment rod 800 in the guide plane E and/or parallel thereto. By this means, the alignment rod 800 can be aligned in particular for monitoring the position of the tibial cutting block 700 and/or for monitoring the extension position of the tibia T parallel to the tibia front edge V. The specific function of the alignment rod 800 will be explained in more detail below.

In the embodiment shown, the alignment rod 800 is assigned a second indicating device A2. The second indicating device A2 is configured for indicating a second angular position $\alpha2$ of the alignment rod 800 with respect to the pivot axis S. In the present case, the second indicating device A2 is a scale with a plurality of scale lines (without reference sign). The scale lines are provided here on the second fastening device 200, more precisely: on the main body 201 thereof. In addition, there is a reading mark, not shown specifically, the latter also being able to be formed, for example, by the alignment rod 800 itself.

An exemplary use of the surgical instrument 1 for positioning the tibial cutting block 700 will be explained below.

The positioning takes place on the basis of a configuration in which the distal femoral cutting block 600 is already fixed to the distal femur F in a manner known to a person skilled in the art. That is to say, the femoral cutting block 600 which is already fixed serves as a reference. The guide slot 601 extends here mediolaterally and anteroposteriorly. A rotational alignment of the guide slot 601 with respect to an anteroposterior axis determines a varus/valgus alignment of the distal femoral cut to be applied. In the present case, it is assumed that the varus/valgus alignment is 0°. The guide slot 601 is consequently oriented parallel to a distal condyle line of the distal femur F. The surgical instrument 1 can be used in particular to transfer a varus/valgus alignment which has already been undertaken femorally to the tibial cutting block 700, more precisely: to the guide slot 701 thereof.

For this purpose, first of all the tibial cutting block 700 is fastened releasably to the second fastening device 200 in the previously described manner. The surgical instrument 1 is then referenced femorally together with the tibial cutting block 700 fastened thereto. For this purpose, the first fastening device 100 is fastened releasably to the femoral cutting block 600 which is already fixed femorally. This is undertaken in the previously described manner, i.e. the plug-in element 101 is plugged posteriorly into the guide slot 601. The configuration shown with reference to FIGS. 1 to 4 is produced by this means.

In this (exemplary) configuration, the femur F and the tibia T are in (full) extension and enclose an angle of 180°. On the basis of such a (full) extension, the adjustment of the sagittal inclination of the guide slot 701 takes place as follows:

First of all, the center point M of the circular arc guide 300 is positioned in a manner adapted to the anatomy of the patient. This positioning takes place by means of the first linear guide 400. When the circular arc guide 300 is shifted along the first guide path L1 in the posterior direction, the center point M moves posteriorly. Conversely, an anteriorly directed relative movement of the circular arc guide 300 in relation to the first fastening device 100—and therefore to the femoral cutting block 600—brings about an anterior shifting of the center point M. It goes without saying that the plug-in element 101 always remains plugged into the guide slot 601 here. The center point M is ideally positioned centrally with respect to a (mechanical) tibial axis, not shown specifically. With such a positioning of the center point M, it is avoided that adjustment of the inclination of the tibial cutting block 700 is simultaneously associated with an inadvertent change in a proximodistal position with respect to the tibia (tibial cutting height).

After the center point M has been positioned via the previously described adjustment of the first linear guide 400, the tibial cutting block 700 is positioned anteriorly lying against the tibia T. The second linear guide 500 ensures that the disposition always meets requirements. The tibial cutting block 700 can be raised or lowered depending on prevailing dimensions of the tibia T by means of the second fastening device 200 being shifted along the second guide axis L2.

In a further step, the actual adjustment of the sagittal inclination of the guide slot 701, i.e. the slope, takes place. In FIGS. 1 to 4, the slope is 0°, and therefore the guide slot 701 of the tibial cutting block 700 is oriented plane-parallel to the guide slot 601 of the femoral cutting block 600. The first angular position $\alpha1$ (FIG. 1) represents the aforementioned slope here. The slope can be adjusted via the circular arc guide 300. The adjusted value can be read by means of the first indicating device A1. The previous positioning of the center point M on the tibial axis means that the tibial cutting height is not changed here.

The alignment rod 800 serves here firstly for monitoring the full extension. With a full extension and parallel alignment of the alignment rod 800 with respect to the tibia front edge V, the second angular position $\alpha2$ here is 0°.

The alignment rod 800 together with the two indicating devices A1, A2 also permits a flexion/extension correction. If a precise extension is not intended to be present, this can be determined by means of the alignment rod 800 and the second indicating device A2 and compensated for via a corresponding adjustment of the slope at the second indicating device A1. For explanatory purposes, the exemplary situation illustrated in FIG. 5 will be described below.

Figure 1:
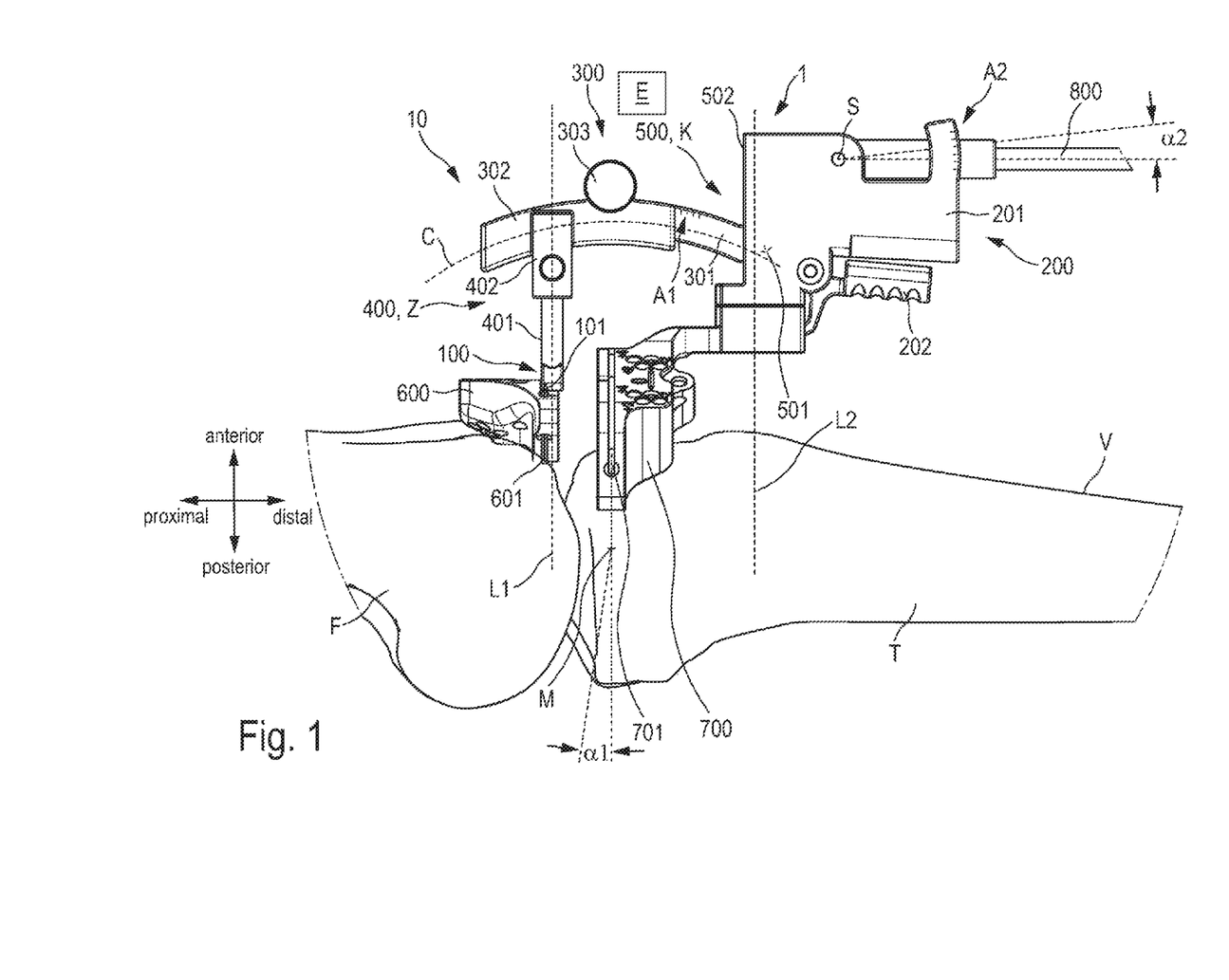
FIG. 1 shows a schematic side view of an embodiment of a surgical instrument according to the present disclosure in an intraoperative situation in which the surgical instrument is fastened releasably at one end to a distal femoral cutting block and at the other end to a proximal tibial cutting block.
Figure 2:
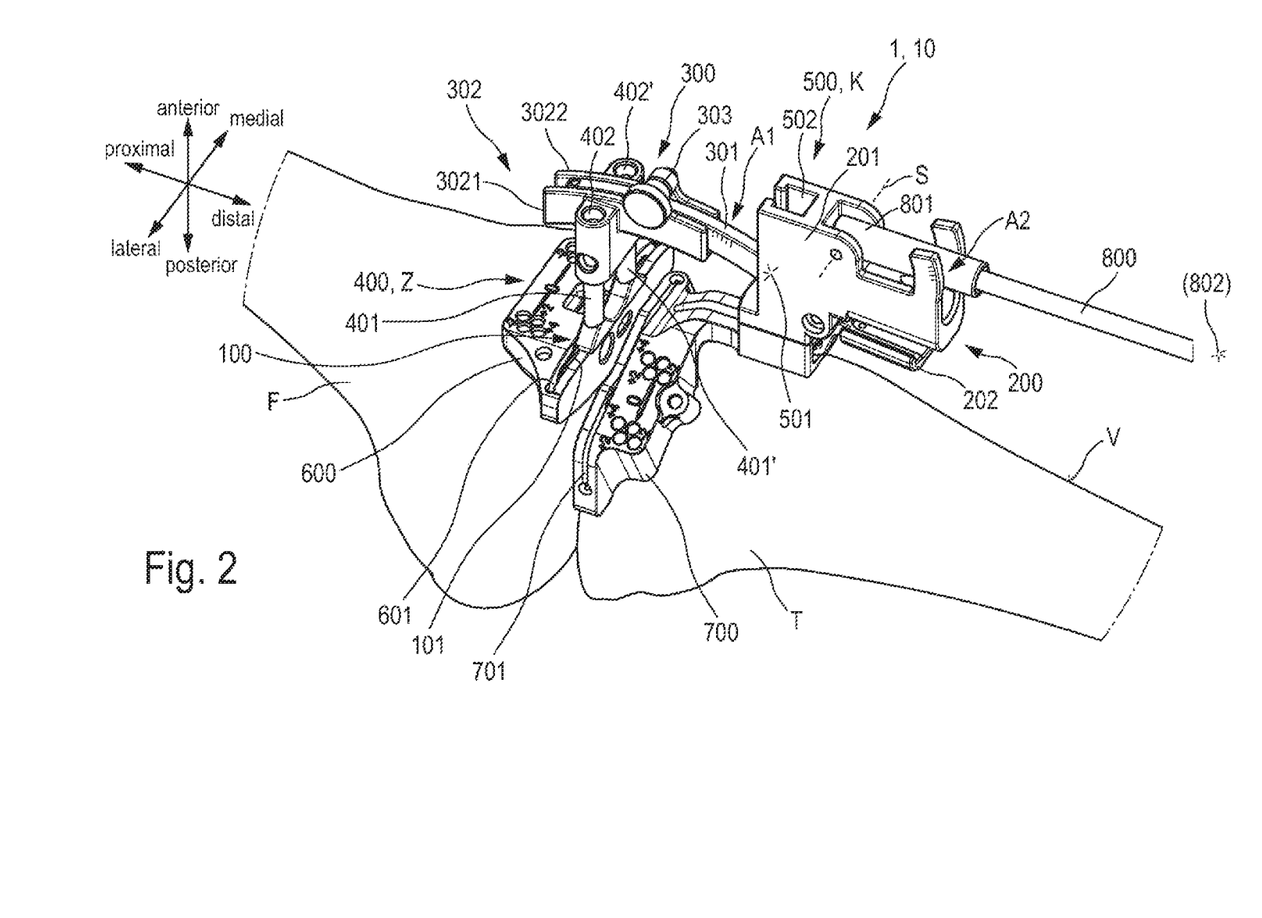
FIG. 2 shows a schematic perspective view of the intraoperative situation shown in FIG. 1.
Figure 3:
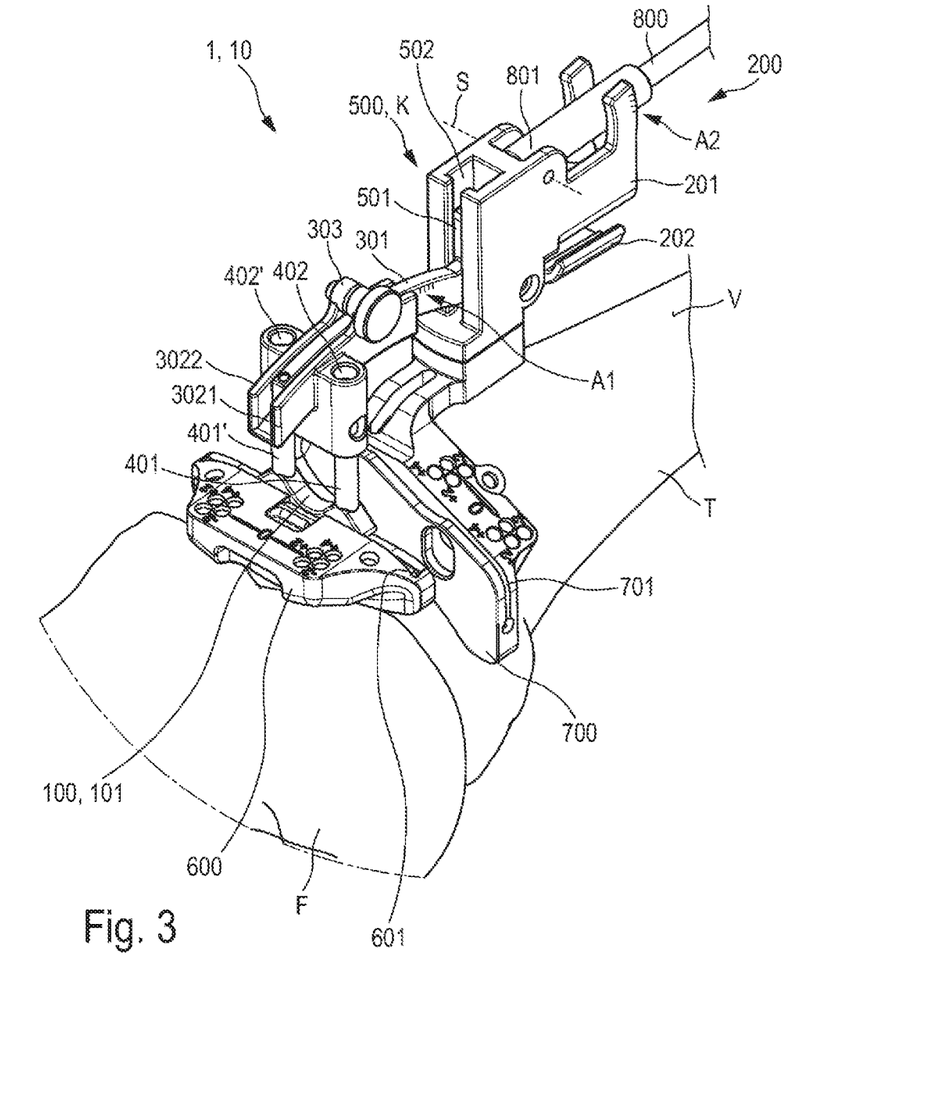
FIG. 3 shows a further schematic perspective view of the intraoperative situation shown in FIGS. 1 and 2.
Figure 4:
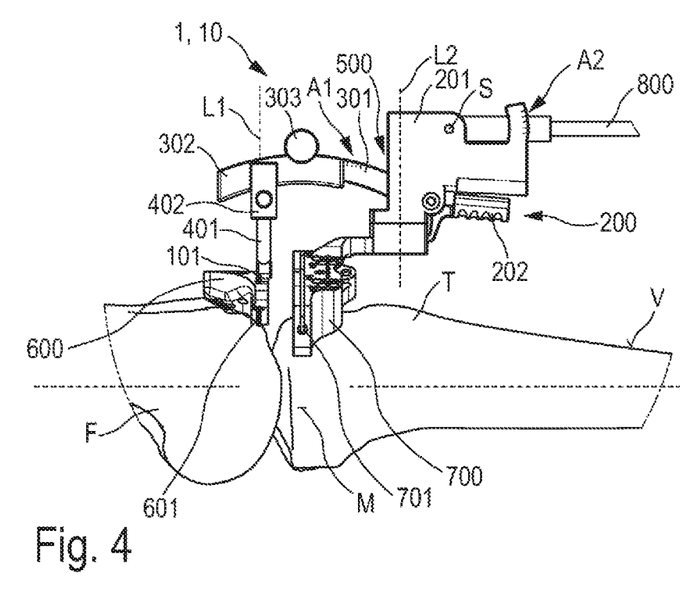
FIG. 4 shows the intraoperative situation in a schematic side view.
Figure 5:
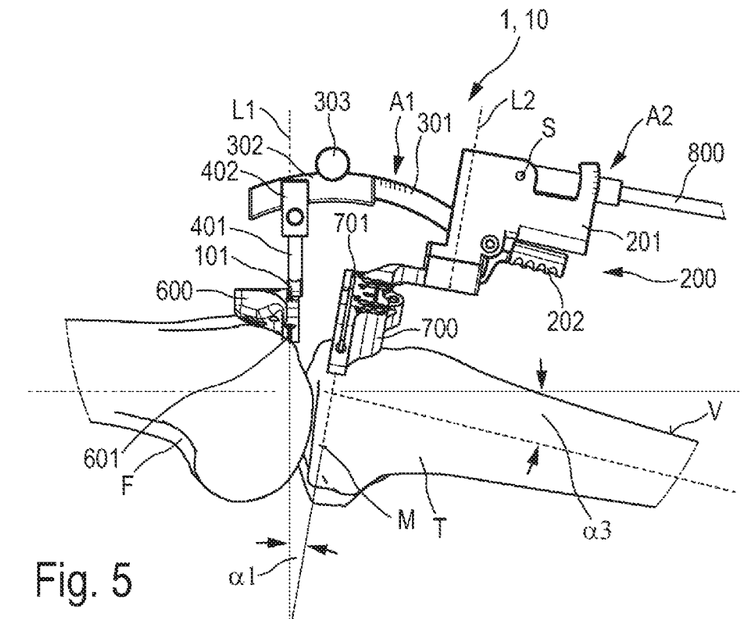
FIG. 5 shows a schematic side view of the surgical instrument in a further intraoperative situation in which the tibial cutting block is aligned inclined sagittally by means of the surgical instrument.

In the situation shown with reference to FIG. 5, there is no full extension. Instead, the tibia T is angled by an angle $\alpha3$ relative to the femur F. The surgical instrument 1 permits the angle $\alpha3$ to be taken into consideration in the adjustment of the slope. For this purpose, first of all the surgical instrument 1 together with the tibial cutting block 700 is connected in the previously described way to the femoral cutting block 600 that has already been fixed. The circular arc guide 300 is then adjusted in such a manner that the indicating device A1 indicates a first angular position $\alpha1$ which represents a slope of 0°. The actual slope here is not 0°—because of the flexion which is present. The angle $\alpha3$ in which the alignment rod 800 is aligned parallel with respect to the tibia front edge V is then determined. The angle $\alpha3$ can be read at the second indicating device A2. The corresponding angle is then adjusted at the circular arc guide 300. This has the effect that the guide slot 701—despite the deviation from full extension—is adjusted orthogonally with respect to the tibia front edge V and therefore to a slope of 0°. Starting from said (main) adjustment, a further adaptation of the slope can be carried out via a corresponding shifting of the circular arc guide 300.

The invention claimed is:

1. A surgical instrument system for use in a knee joint replacement operation, the surgical instrument system comprising:

A. a surgical instrument comprising:
i. a first fastening device configured for releasably fastening to a reference component attached to a distal femur;
ii. a second fastening device spaced apart distally from the first fastening device and configured for releasably fastening to a tibial cutting block for cutting guidance on a proximal tibia;
iii. a circular arc guide connected at a first end to the first fastening device and at a second end to the second fastening device, and by which the second fastening device is linearly movable relative to the first fastening device and guided in a sagittal guide plane along a circular-arc-shaped guide path;
iv. a first linear guide, by which the circular arc guide is connected to the first fastening device and is linearly movable relative to the circular arc guide and guided in the sagittal guide plane along a first guide path which is elongate anteroposteriorly; and
v. a second linear guide, by which the second fastening device is connected to the circular arc guide and is linearly movable relative to the circular arc guide and guided in the sagittal guide plane along a second guide path which is elongate anteroposteriorly, and
B. a reference component releasably fastened to the first fastening device of the surgical instrument; and
C. a tibial cutting block releasably fastened to the second fastening device of the surgical instrument.

2. The surgical instrument system according to claim 1, further comprising an alignment rod configured for aligning on an anterior edge of the tibia, wherein the alignment rod is mounted on the second fastening device so as to be pivotable relative to the second fastening device about a pivot axis oriented orthogonally to the sagittal guide plane.

3. The surgical instrument system according to claim 2, further comprising at least one of:
a first indicating device configured for indicating a first angular position of the second fastening device with respect to the circular-arc-shaped guide path; and
a second indicating device configured for indicating a second angular position of the alignment rod with respect to the pivot axis.

4. The surgical instrument system according to claim 2, wherein the second fastening device comprises a main body on which the following elements are arranged:
a fastening element configured for releasably fastening to a fastening portion of the tibial cutting block;
a guide element of the second linear guide; and
the alignment rod.

5. The surgical instrument system according to claim 1, wherein the circular arc guide comprises at least one guide rod that is curved and a guide receptacle in which the at least one guide rod is accommodated in a slidably guided manner, wherein the guide receptacle is connected to the first linear guide and the at least one guide rod is connected to the second linear guide, or vice versa.

6. The surgical instrument system according to claim 5, wherein at least one of:
the guide receptacle is connected to the first linear guide and has a first guide element; and
the at least one guide rod is connected to the second linear guide and has a second guide element.

7. The surgical instrument system according to claim 1, wherein the first linear guide is a cylinder guide and has at least one cylinder element, which is elongate anteroposteriorly, and a cylinder receptacle in which the at least one cylinder element is accommodated in a slidably guided manner.

8. The surgical instrument system according to claim 7, wherein the at least one cylinder element is connected immovably to the first fastening device, and the cylinder receptacle is connected immovably to the circular arc guide.

9. The surgical instrument system according to claim 1, wherein the second linear guide is a slotted guide mechanism and has a slotted guide block and a slotted guide slot which is elongate anteroposteriorly and in which the slotted guide block is accommodated in a slidably guided manner.

10. The surgical instrument system according to claim 9, wherein the slotted guide block is connected immovably to the circular arc guide, and the slotted guide slot is formed on the second fastening device.

11. The surgical instrument system according to claim 1, wherein the first fastening device has at least one plug-in element configured for releasably plugging together with a complementary reference geometry of the reference component.

12. The surgical instrument system according to claim 1, further comprising a fixing device configured for fixing movability of the circular arc guide.

* * * * *